US010734095B2

(12) United States Patent
Agrawal et al.

(10) Patent No.: US 10,734,095 B2
(45) Date of Patent: Aug. 4, 2020

(54) SYSTEMS AND METHODS FOR PRIORITIZING VARIANTS OF UNKNOWN SIGNIFICANCE

(71) Applicant: KONINKLIJKE PHILIPS N.V., Eindhoven (NL)

(72) Inventors: Vartika Agrawal, White Plains, NY (US); Nevenka Dimitrova, Pelham Manor, NY (US)

(73) Assignee: Koninklijke Philips N.V., Eindhoven (NL)

(*) Notice: Subject to any disclaimer, the term of this patent is extended or adjusted under 35 U.S.C. 154(b) by 1042 days.

(21) Appl. No.: 15/221,672

(22) Filed: Jul. 28, 2016

(65) Prior Publication Data
US 2017/0032081 A1 Feb. 2, 2017

Related U.S. Application Data

(60) Provisional application No. 62/198,191, filed on Jul. 29, 2015.

(51) Int. Cl.
G01N 33/48 (2006.01)
G01N 33/50 (2006.01)
G16B 20/00 (2019.01)
G16B 40/00 (2019.01)
G06N 7/00 (2006.01)

(52) U.S. Cl.
CPC ............ G16B 20/00 (2019.02); G06N 7/005 (2013.01); G16B 40/00 (2019.02)

(58) Field of Classification Search
None
See application file for complete search history.

(56) References Cited

U.S. PATENT DOCUMENTS

| 2005/0043894 | A1* | 2/2005 | Fernandez | A61B 5/0215 702/19 |
| 2010/0304989 | A1* | 12/2010 | Von Hoff | C12Q 1/6841 506/9 |
| 2012/0059594 | A1* | 3/2012 | Hatchwell | C12Q 1/6827 702/19 |
| 2012/0109615 | A1 | 5/2012 | Yun et al. | |
| 2012/0303292 | A1* | 11/2012 | Friesner | G16C 20/50 702/30 |
| 2014/0278135 | A1* | 9/2014 | Pruss | G16B 20/00 702/19 |
| 2014/0310215 | A1 | 10/2014 | Trakadis | |
| 2015/0066378 | A1 | 3/2015 | Robinson et al. | |
| 2016/0253452 | A1 | 9/2016 | Karbassi et al. | |

FOREIGN PATENT DOCUMENTS

WO 2013070634 A1 5/2013
WO WO-2015061422 A1 * 4/2015

OTHER PUBLICATIONS

The Cancer Genome Atlas Research Network, "The cancer genome atlas pan-cancer analysis project." Nature Genetics, vol. 45 , pp. 1113-1120. (Year: 2013).*
Benjamin J Raphael et al: "Identifying driver mutations in sequenced cancer genomes: computational approaches to enable precision medicine", Genome Med, Biomed Central Ltd, London, UK,vol. 6, No. 1, Jan. 30, 2014 (Jan. 30, 2014), pp. 1-17.

* cited by examiner

Primary Examiner — Russell S Negin

(57) ABSTRACT

The present disclosure describes systems and methods for generating a priority score for a variant of a gene based on its potential significance to a disease. Priority scores may be calculated for multiple variants, and the variants may be ranked based on the generated priority scores.

18 Claims, 2 Drawing Sheets

SYSTEMS AND METHODS FOR PRIORITIZING VARIANTS OF UNKNOWN SIGNIFICANCE

This application claims the benefit of U.S. Provisional Patent Application No. 62/198,191, filed on Jul. 29, 2015 which is hereby incorporated by reference herein.

BACKGROUND

A major challenge faced by researches in genomics worldwide is determining how to analyze the enormous amount of data provided by next generation sequencing machines. It is challenging to process the data and translate it into clinically relevant information that can be used in the diagnosis and therapy of diseases. The genome in its entirety is still not fully understood. One challenge is determining the effects of variants of unknown significance.

Several, hundreds, or even thousands of variants of a sequence for a gene may exist. A significant portion of these variants may not have an effect on the function or expression of the gene. However, some of the variants may have an impact on a disease state such as cancer. These variants may be useful for determining which therapies may be effective for treating a particular disease (e.g., a tumor exhibiting a particular variant may be more susceptible to a drug than tumors without the variant) and/or for finding targets for new therapies. Determining which variants may be useful for research and/or treatment and which do not have a significant effect remains a challenge.

Various algorithms have been developed to predict the functional effect of variants. Each algorithm has its own scores to categorize variants in classes such as Benign, Deleterious, Potentially deleterious, Tolerant etc. Each of these algorithms has its metrics to classify variants into the categories mentioned above. However, there is discrepancy in the results of these algorithms.

SUMMARY OF THE INVENTION

An example method according to an embodiment of the disclosure may include receiving a genetic sequence from a memory, the genetic sequence may include a variant of a gene; receiving a pathogenicity score for the variant of the gene, wherein the pathogenicity score may indicate a likely pathogenicity of the variant; calculating, with at least one processor, a prevalence of the variant in a disease data set stored in a database accessible to the at least one processor; calculating, with the at least one processor, a prevalence of the variant in a healthy population data set stored in the database; calculating, with the at least one processor, a mutation rate for the gene in the disease data set stored in the database; calculating, with the at least one processor, a mutation rate for the gene in the healthy population data set stored in the database; generating a priority score for the variant, based at least in part, on the pathogenicity score, the prevalences of the variant in the disease data set and the healthy population data set, and the mutation rates for the gene in the disease data set and the healthy population data set; and providing the priority score to a user, wherein the priority score may indicate a significance of the variant to the disease.

An example system according to an embodiment of the disclosure may include a processor, a memory accessible to the processor, the memory may be configured to store a genetic sequence in digital form, wherein the genetic sequence may include a variant of a gene, a database accessible to the processor, and a display coupled to the processor, wherein the processor may be configured to: receive the genetic sequence from the memory, the genetic sequence may include a variant of a gene, calculate a pathogenicity score for the variant of the gene, wherein a high pathogenicity score may indicate a higher likelihood of pathogenicity of the variant, calculate a disease gene mutation score for the gene, based at least in part, on mutation rates for the gene in a disease stored in the database, wherein a high disease gene mutation score may indicate a higher likelihood of significance of the gene to a disease, calculate a disease frequency score for the variant, based at least in part, on frequencies of the variant in the disease stored in the database, wherein a high disease frequency score may indicate a higher likelihood of significance of the variant to the disease, calculate a healthy frequency score for the variant, based at least in part, on frequencies of the variant in a healthy population stored in the database, wherein a high healthy frequency score may indicate a lower likelihood of significance of the variant to the disease, calculate a healthy gene mutation score for the gene, based at least in part, on rates for the gene in the healthy population stored in the database, wherein a high healthy gene mutation score may indicate a lower likelihood of significance of the gene to the disease, combine the pathogenicity score, disease gene mutation score, disease frequency score, healthy frequency score, and healthy gene mutation score together to produce a priority score for the variant, and provide the priority score to the display, wherein the priority score may indicate a significance of the variant of the gene to the disease.

DETAILED DESCRIPTION

Figure 1:
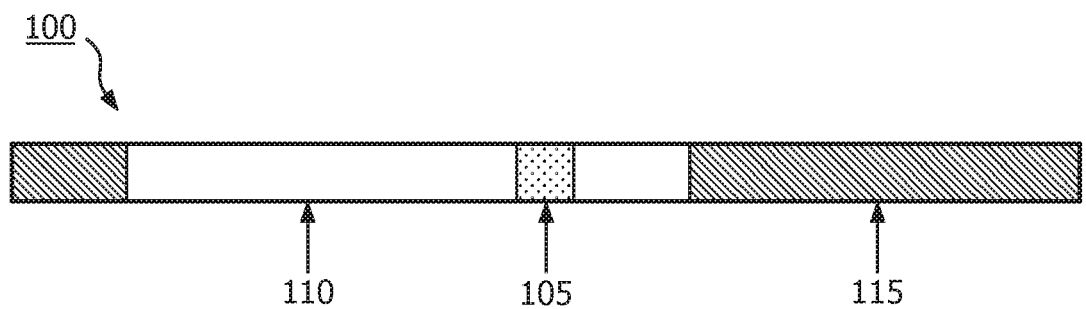
FIG. 1 is a diagram of a genetic sequence according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Example methods and systems are described herein to integrate various variant pathogenicity scores which are, in general, highly discordant. The scoring schemes described herein may provide a more robust and/or reliable score that may be used to prioritize variants of unknown significance with a higher sensitivity and specificity than conventional scoring algorithms.

The prevalence of the variant across healthy populations and disease affected populations may be used to associate a variant with pathogenicity by eliminating variants that are also highly prevalent in the healthy populations. The addition of population-level information may eliminate or reduce false positives of variants which may be predicted deleterious by conventional scoring algorithms but are also found frequently in healthy populations.

There are genes which are highly variable, that is, they have a higher mutation rate than other genes. Variants of highly variable genes may be less significant than variants in genes with lower mutation rates. The background mutation rates for genes may be used to lower the pathogenicity score for a variant found in a highly variable gene.

The methods and systems described herein may include a composite scoring method to produce a priority score for variants of unknown significance by integrating currently used functional prediction algorithms along with factors that are important in predicting the pathogenicity of a particular variant. For example, algorithms such SIFT, Polyphen, LRT, and Mutation Taster have various scoring criteria and methods and may be used to generate one or more scores that may be used to produce the final priority score for a variant.

The priority score for a variant calculated by methods and systems described herein may be used to prioritize variants of one or more genes. The priority scores may be based on multiple measures that may reduce conflicting scores reflecting the probability of a variant being pathogenic and/or significant to a disease.

FIG. 1 is a diagram of a genetic sequence 100 according to an embodiment of the disclosure. The genetic sequence 100 may be a sequence for a gene, multiple genes, or a portion of a gene. The genetic sequence 100 may include a variant 105 of a gene. The variant 105 may be a point mutation or may include multiple base pairs. The variant 105 may be included in an exome 110 portion of the sequence 100. The exome 110 may encode for one or more amino acids. The genetic sequence 100 may also include one or more intron 115 portions. In some embodiments, the genetic sequence 100 may be selected to exclude one or more intron 115 portions.

The variant 105 in the gene may cause one or more amino acids to be substituted with alternative amino acids and/or removed from a protein synthesized from that portion of the genetic sequence 100. The change in the amino acids encoded by the gene due to the variant 105 may affect the function and/or structure of one or more proteins. The variant may cause over or under expression of one or more proteins. These effects may be deleterious, contributing to the pathogenicity of the variant 105. For example, a variant in the p53 gene may cease production of a protein or cause production of a malformed protein responsible for stopping mutated cells from dividing. Without the active form of the protein, the mutated cells may divide and form tumors.

If the variant 105 and its effects are highly associated with a particular disease (e.g., cancer, autoimmune disorder), the variant 105 may be used to select targeted therapies and/or choose candidates for clinical studies. However, many variants have little to no effect. Many variants may not be specific to diseases or other conditions. A gene may have thousands of variants, but only a small fraction may be potentially clinically relevant (e.g., have a pathogenic effect). Pre-existing algorithms, such as SIFT and Polyphen, attempt to predict the pathogenicity of a variant and assign a pathogenicity score. However, these algorithms may provide conflicting results and over or under predict pathogenicity of a variant. It may be difficult for a system or a user to determine which variants are most significant. Additional factors may be considered which may improve the pre-existing algorithms for determining pathogenicity of a variant and prioritizing multiple variants.

Figure 2:
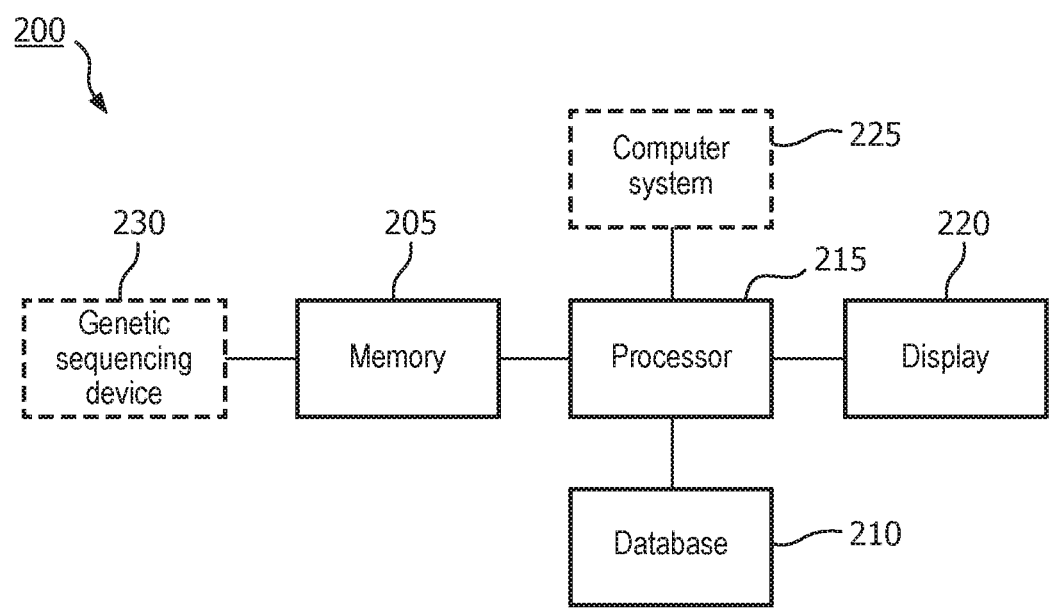
FIG. 2 is a functional block diagram of a system according to an embodiment of the disclosure.

FIG. 2 is a functional block diagram of a system 200 according to an embodiment of the disclosure. The system 200 may be used to generating a priority score for a variant, which may be a measure of its significance to a disease and/or other condition. A genetic sequence (e.g., the genetic sequence 100 shown in FIG. 1) in digital form may be included in memory 205. The memory 205 may be accessible to processor 215. The processor 215 may include one or more processors. The processor 215 may have access to a database 210 that includes one or more datasets (e.g., The Cancer Genome Atlas (TCGA)). In some embodiments, the database 210 may include one or more databases. The processor 215 may provide the results of its calculations. For example, the results may be provided to a display 220 and/or the database 210. The display 220 may be an electronic display visible to a user. In some embodiments, the system may also include other devices to provide the results, such as a printer. Optionally, processor 215 may further access a computer system 225. The computer system 225 may include additional databases, memories, and/or processors. The computer system 225 may be a part of system 200 or remotely accessed by system 200. In some embodiments, the system 200 may also include a genetic sequencing device 230. The genetic sequencing device 230 may process a biological sample (e.g., genetic isolate of a tumor biopsy, cheek swab) to generate a genetic sequence and produce the digital form of the genetic sequence.

The processor 215 may be configured to calculate a prevalence of a variant in one or more populations stored in one or more datasets, which may be stored in the database 210. The processor 215 may be configured to calculate a mutation rate of a gene in one or more populations stored in one or more datasets, which may be stored in the database 210. The processor 215 may be configured to generate a priority score based, at least in part, on the calculated prevalence, mutation rate, and/or a received pathogenicity score. In some embodiments, the processor 215 may be configured to combine one or more pathogenicity scores to generate the priority score. In some embodiments, the processor 215 may be configured to determine the zygosity of a variant. The processor 215 may be configured to provide the priority score to the display 220, the database 210, memory 205, and/or computer system 225. In some embodiments, when the processor 215 includes more than one processor, the processors may be configured to perform different calculations to determine the priority score and/or perform calculations in parallel.

In some embodiments, the processor 215 may be configured to calculate a priority score for more than one variant. In these embodiments, the processor 215 may be configured to rank the variants based, at least in part, on the priority score of each variant. In some embodiments, one or more genetic sequences in the memory 205 may be added to the database 210. The genetic sequences may be added to one or more datasets in the database 210 and used to dynamically update the calculation of a priority score, ranking of the variants, and/or used in subsequent calculations of a priority score of a variant.

In some embodiments, the processor 215 may be configured to apply Dempster-Shafer theory on the pathogenicity score and other calculations described above to generate a priority score for a variant.

The system 200 may allow for faster determination of the variants most significant to a disease or other condition by improving the prioritization of the variants. This may lead to faster analysis of the most significant variants (e.g., protein folding analysis, gene expression). Existing systems provide a high percentage of false-positives for significance of variants, requiring extensive additional calculations, and/or time consuming review which reduces the ability to determine the most significant variants. Determination of the most significant variants may allow the system 200, other systems, and/or users to make treatment and/or research decisions based on the most significant variants. The system 200 may be used in a research lab, a hospital, and/or other environment. A user may be a disease researcher, a doctor, and/or other clinician.

Figure 3:
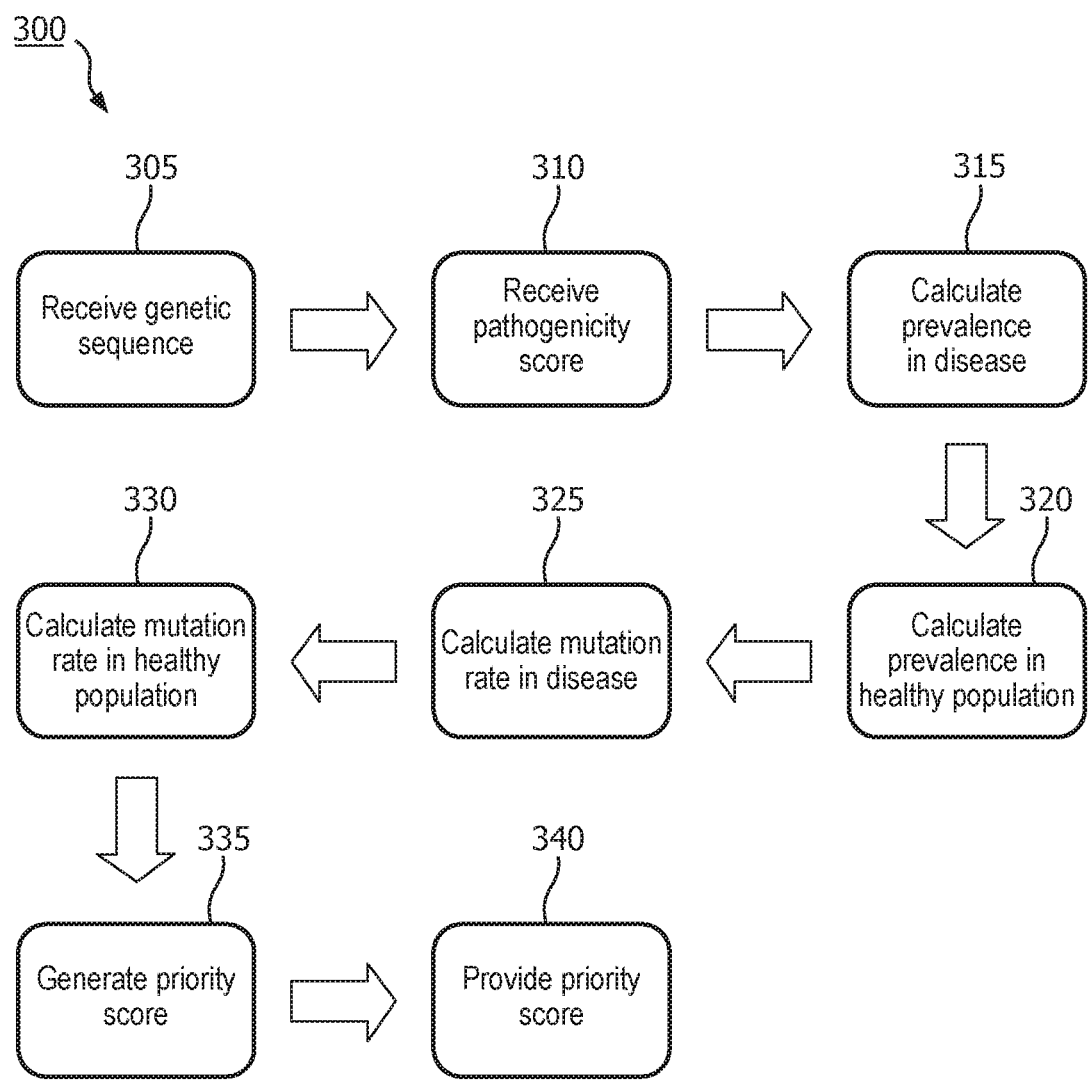
FIG. 3 is a flow chart of a method according to an embodiment of the disclosure.

FIG. 3 is a flow chart of a method 300 for generating a priority score for a variant according to an embodiment of the disclosure. In some embodiments, the method 300 may be performed by a system such as system 200 shown in FIG. 2. A genetic sequence for a variant may be received at Block 305. The genetic sequence may be in digital form and provided to a memory. The genetic sequence may be provided by a next generation sequencing device or another source (e.g., database, portable hard drive, Internet). A pathogenicity score or scores for the variant may be received at Block 310. The pathogenicity score may have been calculated using a known algorithm such as SIFT, Polyphen, LRT, Mutation Taster, and/or other algorithm. When more than one pathogenicity score is received, in some embodiments, the scores may be combined into a single pathogenicity score (e.g., averaging, normalized and summed, or normalized and multiplied).

At Block 315, the prevalence of the variant in a disease may be calculated. Prevalence may be calculated by a percentage of disease instances where the variant is present, a total number of instances of the variant in a sample of genetic sequences, and/or other method. The prevalence may be calculated by determining the frequency of occurrence of the variant in a dataset of genetic sequences of the disease. At Block 320, the prevalence of the variant in a healthy population may be calculated. The prevalence of the variant in the healthy population may be calculated in a similar manner as the prevalence of the variant in the disease. For example, prevalence may be determined by the percentage of instances where the variant is present in the healthy population and/or the total number of instances of the variant in a sample of genetic sequences from the healthy population.

Datasets of sequences for one or more genes may be used to determine the prevalence of a variant in one or more populations. A population may be a population of individuals (e.g., humans, mice) or cells (e.g., hepatic, HeLa). Although not shown in FIG. 3, additional populations and/or sub-populations may be analyzed (e.g., multiple species, ethnic group, gender). The greater the relative prevalence of the variant in the disease compared to the prevalence in the healthy population, the more likely the variant is significant to the disease. An example of a dataset of sequences is The Cancer Genome Atlas (TCGA). TCGA may be used as a dataset for a disease population. Another example of a dataset of sequences is the 1,000 Genomes Project. This dataset may be used for a health population. Other datasets may also be used.

The datasets may also be used to determine the prevalence of mutations in a gene. The prevalence of mutations in a gene may correspond to a mutation rate of the gene. At Block 325, the mutation rate of a gene including the variant is calculated, followed by calculating the mutation rate of a gene including the variant in a healthy population at Block 330. Mutation rate may be calculated using substitution rates, mutation accumulation lines, phylogenetic methods, and/or other methods. The greater the relative mutation rate of the gene in the disease compared to the mutation rate in the healthy population, the more likely mutations in the gene are significant to the disease. Mutations in a gene with a low mutation rate in both healthy and disease populations may be more significant than mutations in a gene with a high mutation rate in both healthy and disease populations.

The calculated prevalence of the variant and mutation rates in Blocks 315-330 may be used to modify the pathogenicity score calculated at Block 310. A priority score may be generated at Block 335. The priority score may be the pathogenicity score adjusted by the variant prevalence and mutation rates. The adjustments may reduce the over and/or under-estimation of pathogenicity calculated by a pre-existing algorithm. The priority score may then be provided to a user at Block 340. The priority score for the variant may be provided to a digital display, a print-out, a non-transitory computer readable medium, and/or other device.

Method 300 may be performed for multiple variants of one or more genes. The variants may then be ranked based on their priority scores. The higher the priority score, the more likely the variant is significant to the disease. For example, variants and their associated priority scores may be provided as a list to a user. The list may be ordered and/or ranked with the variants having the highest priority score at the top of the list. This may allow the user to quickly determine which variants are most likely to be significant. In some embodiments, only those variants having a priority score above a desired threshold score may be provided to a user. A user may select a therapy and/or candidates for a clinical trial based on the priority scores of the variants.

In some examples, one or more of the highest ranking variants may be provided to a processor, such as processor 215 shown in FIG. 2. The processor may determine a change in expression of a protein, based at least in part, on the priority score. The change in expression of a protein may be used by clinicians to select a therapy, prioritize targets for drug discovery, and/or other applications.

Additional factors may be considered to improve the pathogenicity score. In some embodiments, the zygosity of a variant may be analyzed. A heterozygous variant may modify the pathogenicity score to generate a lower priority score or may not modify the pathogenicity score. A homozygous variant may modify the pathogenicity score to generate a higher priority score. That is, a homozygous variant (the variant occurs in both copies of the chromosome) may be more significant to a disease than a heterozygous variant. In some embodiments, the zygosity of the variant may be 2 if the variant is homozygous and 1 if the variant is heterozygous.

In some embodiments, as described briefly above, the prevalence of a variant in a sub-population may be calculated, such as a germline and/or functional domain dataset, to modify the pathogenicity score to generate the priority score. For example, with a germline dataset, a variant that occurs infrequently in a Chinese population may be more significant to a disease in a Chinese patient, but may be less significant to a disease in a European population where the variant occurs more frequently in healthy Europeans. In another example, the prevalence of a variant in a functional domain such as a cancer-specific functional domain may be calculated.

An exemplary equation for calculating a priority score according to an embodiment of the disclosure is:

$$\text{Score}=D_p+D_s+D_m+D_l+H_h+G_{tcga}+V_{tcga}+V_{1kg}+G_{1kg}^{gp}+G_{1kg}^{1p}+Dom_{TCGA}+Dom_{1kg} \quad \text{Equation (1)}$$

Where:
$D_p$ is Normalized polyphen pathogenicity score
$D_s$: Normalized sift pathogenicity score
$D_m$: Normalized mutation taster pathogenicity score
$D_l$: Normalized LRT pathogenicity score
$H_h$: Zygosity score.
$G_{tcga}$: The frequency of mutations within this gene in the TCGA
$V_{tcga}$: The frequency of this variant within the TCGA
$V_{1kg}$: The frequency of this variant within the 1,000 Genomes Project population
$G_{1kg}^{gp}$: The frequency of mutations within this gene in the 1 KG across all populations
$G_{1kg}^{1p}$: The frequency at mutation level at a single population level (if the original population for this patient is known)
$Dom_{1kg}$: Frequency of mutation within a functional domain in germline
$Dom_{TCGA}$: Frequency of mutation within a functional domain The example shown in Equation (1) is a forgiving priority score calculation. Equation (1) may be favorable when a large number of variants for review is desired. Equation (1) considers scores from the pathogenicity score algorithms in an additive context and more high priority scores for variants may be generated.

A second exemplary equation for calculating a priority score according to an embodiment of the disclosure is:

$$\text{Score}=D_p*D_s*D_m*D_l+H_h+G_{tcga}+V_{tcga}+V_{1kg}+G_{1kg}^{gp}+G_{1kg}^{1p}+Dom_{TCGA}+Dom_{1kg} \quad \text{Equation (2)}$$

The variable definitions are the same as those provided for Equation (1). Equation (2) is a penalizing priority score calculation. This equation may be favorable when a small number of variants for review is desired. Equation (2) considers scores from the pathogenicity score algorithms in a multiplicative context, and fewer high priority scores for variants may be generated.

Equations (1) and (2) are provided as illustrative, non-limiting examples. Other priority score calculations may be possible. For example, Equations (1) or (2) may include more or fewer pathogenicity scores.

In an alternative embodiment, Dempster-Shafer theory may be used to combine the pathogenicity scores, prevalences, and mutation rates into a priority score. Dempster-Shafer theory combines evidence from disparate sources and derives a degree of belief represented by a belief function, which may be used as a priority score. Other methods of generating the priority score may be used.

Although the specification describes methods and systems for determining the variants most significant to a disease, other applications are possible. For example, variants most significant to disease resistance, physical characteristics, biocompatibility, allergies, and/or other traits may be determined.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
    receiving a genetic sequence from a memory, the genetic sequence including a variant of a gene;
    receiving a pathogenicity score for the variant of the gene, wherein the pathogenicity score indicates a likely pathogenicity of the variant;
    calculating, with at least one processor, a prevalence of the variant in a disease data set stored in a database accessible to the processor, wherein the disease data set includes a population that includes a plurality of diseased individuals;
    calculating, with the at least one processor, a prevalence of the variant in a healthy population data set stored in the database, wherein the healthy population data set includes a population that includes a plurality of healthy individuals;
    calculating, with the at least one processor, a mutation rate for the gene in the disease data set stored in the database;
    calculating, with the at least one processor, a mutation rate for the gene in the healthy population data set stored in the database;
    generating a priority score for the variant, based at least in part, on the pathogenicity score, the prevalences of the variant in the disease data set and the healthy population data set, and the mutation rates for the gene in the disease data set and the healthy population data set;
    providing the priority score to a user, wherein the priority score indicates a significance of the variant to the disease;
    based on the priority score, determining a change in expression of a protein;
    based on the change in expression of the protein, selecting a therapy and treating a patient based on the selected therapy.

2. The method of claim 1, wherein the pathogenicity score includes a plurality of pathogenicity scores summed together.

3. The method of claim 1, wherein the pathogenicity score includes a plurality of pathogenicity scores multiplied together.

4. The method of claim 1, wherein the pathogenicity score is a SIFT score, a Polyphen score, LRT score, or a mutation taster score.

5. The method of claim 1, wherein generating the priority score comprises applying a Dempster-Shafer algorithm.

6. The method of claim 1, further comprising:
calculating a mutation rate in a population data set, wherein the population data set is selected to include the patient from which the genetic sequence was acquired; and
generating the priority score based, at least in part, on the mutation rate in the population data set.

7. The method of claim 1, further comprising:
generating a plurality of priority scores for a plurality of variants; and
ranking the plurality of variants based on the plurality of priority scores, wherein a high ranking indicates a high significance to the disease.

8. The method of claim 1, further comprising:
calculating, with the at least one processor, a zygosity of the variant, wherein the zygosity is based at least in part on whether the variant is homozygous or heterozygous; and
generating the priority score based, at least in part, on the zygosity.

9. The method of claim 1, further comprising:
calculating, with the at least one processor a prevalence of the variant in a healthy population germline data set stored in the database; and
generating the priority score based, at least in part, on the prevalence of the variant in the healthy population germline data set.

10. The method of claim 1, further comprising:
calculating, with the at least one processor, a prevalence of the variant in a functional domain disease data set stored in the database; and
generating the priority score based, at least in part, on the prevalence of the variant in the functional domain disease data set.

11. The method of claim 1, further comprising selecting candidates for a clinical trial, based on the priority score.

12. A system comprising:
a processor;
a memory accessible to the processor, the memory configured to store a genetic sequence in digital form, wherein the genetic sequence includes a variant of a gene;
a database accessible to the processor; and
a display coupled to the processor;
wherein the processor is configured to:
receive the genetic sequence from the memory, the genetic sequence including a variant of a gene;
calculate a pathogenicity score for the variant of the gene, wherein a high pathogenicity score indicates a higher likelihood of pathogenicity of the variant;
calculate a disease gene mutation score for the gene, based at least in part, on mutation rates for the gene in a disease stored in the database, wherein a high disease gene mutation score indicates a higher likelihood of significance of the gene to the disease;
calculate a disease frequency score for the variant, based at least in part, on frequencies of the variant in the disease stored in the database, wherein a high disease frequency score indicates a higher likelihood of significance of the variant to the disease;
calculate a healthy frequency score for the variant, based at least in part, on frequencies of the variant in a healthy population of multiple individuals stored in the database, wherein a high healthy frequency score indicates a lower likelihood of significance of the variant to the disease;
calculate a healthy gene mutation score for the gene, based at least in part, on rates for the gene in the healthy population stored in the database, wherein a high healthy gene mutation score indicates a lower likelihood of significance of the gene to the disease;
combine the pathogenicity score, disease gene mutation score, disease frequency score, healthy frequency score, and healthy gene mutation score together to produce a priority score for the variant, wherein the priority score indicates a significance of the variant to the gene to the disease;
based on the priority score, determine a change in expression of a protein;
based on the change in expression of the protein, select a therapy for treating a patient;
provide the selected therapy to the display, and treat the patient with the selected therapy.

13. The system of claim 12, wherein the database includes The Cancer Genome Atlas (TCGA) data.

14. The system of claim 12, wherein the database includes 1,000 Genomes Project data.

15. The system of claim 12, wherein the variant is included in an exome of the genetic sequence.

16. The system of claim 12, wherein the processor is further configured to calculate and normalize a plurality of pathogenicity scores and combine the plurality of pathogenicity scores to calculate the pathogenicity score.

17. The system of claim 12, wherein the processor is further configured to:
calculate a zygosity score for the variant, wherein the zygosity score is based at least in part on whether the variant is homozygous or heterozygous, wherein the zygosity score is higher when the variant is homozygous;
calculate a germline functional domain score for the variant, based at least in part, on frequencies of the variant in the healthy population stored in the database;
calculate a disease functional domain score for the variant, based at least in part, on frequencies of the variant in the disease stored in the database; and
combine the zygosity score, germline functional domain score, and the disease functional domain score with the priority score.

18. The system of claim 12, further comprising a genetic sequencing device configured to provide the genetic sequence in digital form to the memory.

* * * * *